United States Patent [19]

Patterson

[11] 4,212,267
[45] Jul. 15, 1980

[54] INSECT STUDY STATION

[76] Inventor: Irvin G. Patterson, 2730 Hwy. 90 West, Seguin, Tex. 78155

[21] Appl. No.: 967,582

[22] Filed: Dec. 8, 1978

[51] Int. Cl.² ............................................ A01K 67/00
[52] U.S. Cl. ........................................... 119/1; 119/75
[58] Field of Search ................................ 119/1, 15, 17

[56] References Cited

U.S. PATENT DOCUMENTS

| | | |
|---|---|---|
| 948,805 | 2/1910 | Akerlind .................................. 119/1 |
| 2,151,589 | 3/1939 | Falls ........................................ 119/1 |
| 3,626,902 | 12/1971 | Orfei ...................................... 119/15 |
| 3,874,335 | 4/1975 | Galasso ................................. 119/15 |
| 4,106,438 | 8/1978 | Nelson .................................... 119/1 |

Primary Examiner—Hugh R. Chamblee
Attorney, Agent, or Firm—Gunn & Lee

[57] ABSTRACT

An insect study station comprising an elongated transparent cylinder enclosed and supported by a detachable base. The interior of said base having constructed an indentation therein defining a food cup of a configuration affording open access to the transparent cylinder. The upper end of the cylinder is enclosed by an undercap. The undercap telescopically encloses the cylinder and has constructed in the under surface of the undercap a recess which can receive and retain a cotton ball. The circular body of the undercap has constructed through it a series of pie shaped apertures. An overcap telescopingly fits over and encases said undercap. The overcap has constructed in its circular body a series of pie shaped apertures. The dispersal and configuration of the pie-shaped apertures in the undercap and the overcap are of such shape and configuration as to permit access to the cylinder when the apertures are aligned and enclose the cylinder when the apertures are staggered. The primary development incorporated in this invention is the configuration and the detachability of the base and food cup which facilitates the controlled reproduction and segregation of insects' eggs and larvae in the genetic observation and study of insects such as fruit flies.

5 Claims, 7 Drawing Figures

INSECT STUDY STATION

BACKGROUND OF THE INVENTION

1. Field of the Invention

This invention pertains to a small plastic or glass container suitable for feeding and breeding insects for scientific studies such as the fruit fly. The invention pertains to a container or station for ease of breeding, feeding, and retaining insects for study in a laboratory environment.

2. Description of Prior Art

Numerous types of containers have been utilized throughout the years for retaining insects in a laboratory study environment. Some of the early methods utilized were glass jars or bottles having either lid enclosures or enclosed with cotton wads as stoppers. In recent years, with the advent of plastics, numerous refined embodiments of these containers have been developed; some of which have been the subject of patents.

U.S. Patent to Pehr, U.S. Pat. No. 3,587,944, pertains to a small cuplike container having a hinged double flap lid or top for the container.

U.S. Patent to Swanson, U.S. Pat. No. 3,769,936, is essentially a large clear plastic petri dish commonly used in laboratories with the addition of a flap in the lid to facilitate limited access to the dish.

To the best of the knowledge of your applicant, the nearest reference to the present disclosure is U.S. Patent to Galasso, U.S. Pat. No. 3,874,335, which pertains to a large, rectangular enclosure referred to in the patent as a tank with an aperture in the top with the lid which will receive in tight engagement a vial for depositing insects into the study station. Multiple apertures in the bottom of the tank are adapted to receive multiple vials or compartments for varying environments or study. Means are provided for retaining these multiple vials in position in communication with the tank.

One of the principal differences in the present invention and the prior art is providing in the present invention of a detachable food cup enclosing the bottom of a cylindrical sleeve container which facilitates the removal of food and larvae from the cylindrical container which facilitates study of the insects and segregation of generations, particularly of fruit fly larvae for genetic studies. Other modifications in the current invention include provisions for attaching or retaining a series of the cylindrical containers together as well as structural improvements such as providing an improved enclosure cap which facilitates anesthetizing the insects in the container as well as controlling the emission of air or artificial atmosphere to the container. This cap structure involves an overcap and an undercap incorporating a series of slots. Various methods of clips, clip slots, and/or base retainers and base grooves may be incorporated in the structure for attaching a series of cups together.

SUMMARY OF THE INVENTION

This invention comprises a base structure into which is constructed a feed cup. A series of cylindrical sleeves are provided which might be of glass, acrylic, plastic or polyvinyl chloride type structure. The cylinder would normally be transparent while the base and food cup might be translucent or opaque. The cylinder would normally be approximately ¾ to 1¼ inches in diameter and 3½ to 6 inches in length. Small size for experiments; large size for stock cultures. Larger sizes could be available, but are cumbersome. Provision is made in this structure to retain a series of the cylinders on their bases with securing means attaching the bases together. One method of attaching them together would involve a clip constructed in the edge of base 10 which engages a clip slot in an adjacent base. Another method of construction might involve an elongated base retainer having a base lip groove into which the lip of the base intermeshes with a series of the bases or food cups being retained in a base retainer. A series of the transparent or translucent cylinders would slide over the sleeve of the base retaining a series of the cylinders in an upright position on the series of bases. A cap is provided to cover the top end of the cylinder with this cap fitting down into the cylinder with a cap stop contacting the cylinder top with the undercap fitting into the cylinder in a stopper-like engagement. This undercap normally would include a small cotton or other fiber insert to prevent the escape of the insects in the container in the event of the overcap is removed. The overcap fits down over the undercap with each of the caps being constructed with pie-shaped or triangular slots intermittently in their upper surface. A rotation of the overcap will, in effect, close these intermeshing slots forming what amounts to a solid lid closing the container. The principal advantage of this invention over previous containers is the fact that insects such as fruit flies when disturbed tend to fly to the top of the cylinder. The food cup may be removed from the bottom of the cylinder with a minimal number of the insects escaping. Another food cup may be inserted and the food cup containing larvae placed in a new container for their hatching or passing through the pupae stage to create and collect a new generation of fruit flies or other insects.

BRIEF DESCRIPTION OF THE DRAWINGS

For a description of the construction of this invention, attention is invited to the attached drawings where identical symbols will designate identical or equivalent structures throughout the various views and the following detailed description of the construction and operation of the device.

DESCRIPTION OF THE PREFERRED EMBODIMENT

Figure 1:
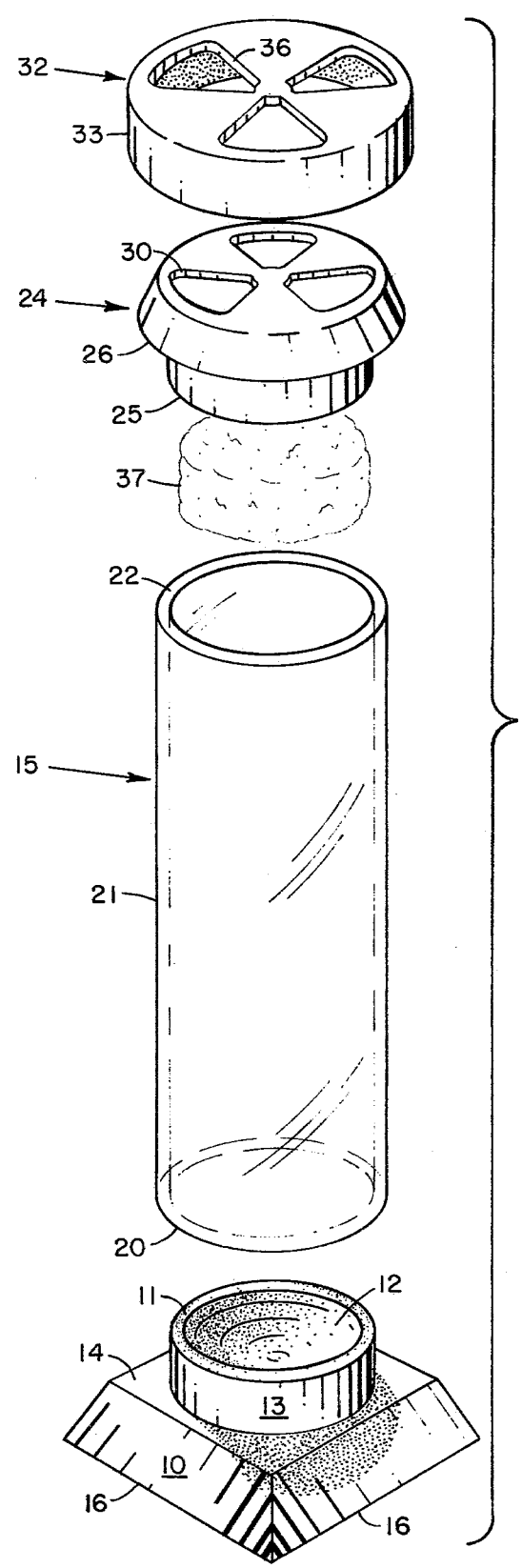
FIG. 1 is an exploded perspective view of one of the cylinders with base and the undercap and overcap comprising one compartment of the device.
Figure 2:
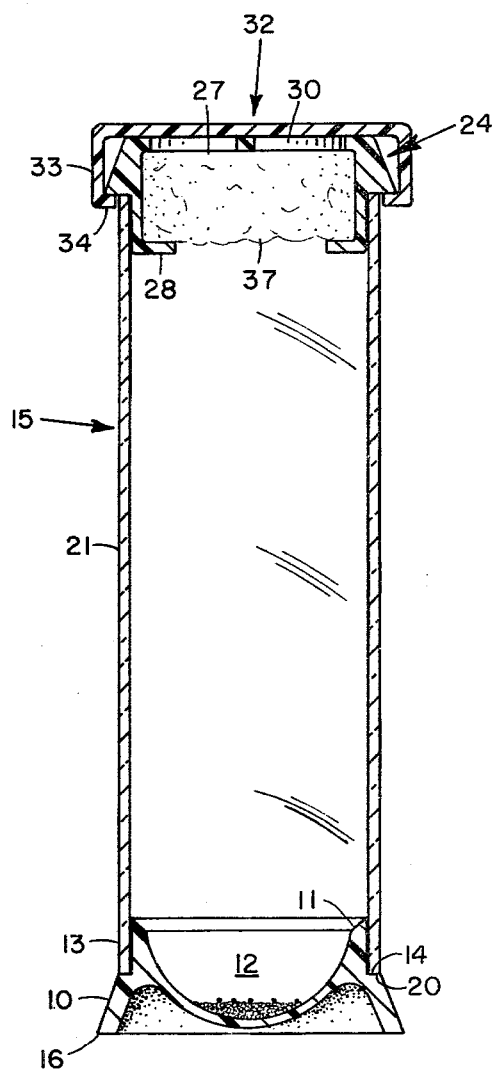
FIG. 2 is an elevated cross-section of one embodiment of the device utilizing a molded base and food cup suggested.
Figures 3A, 3B:
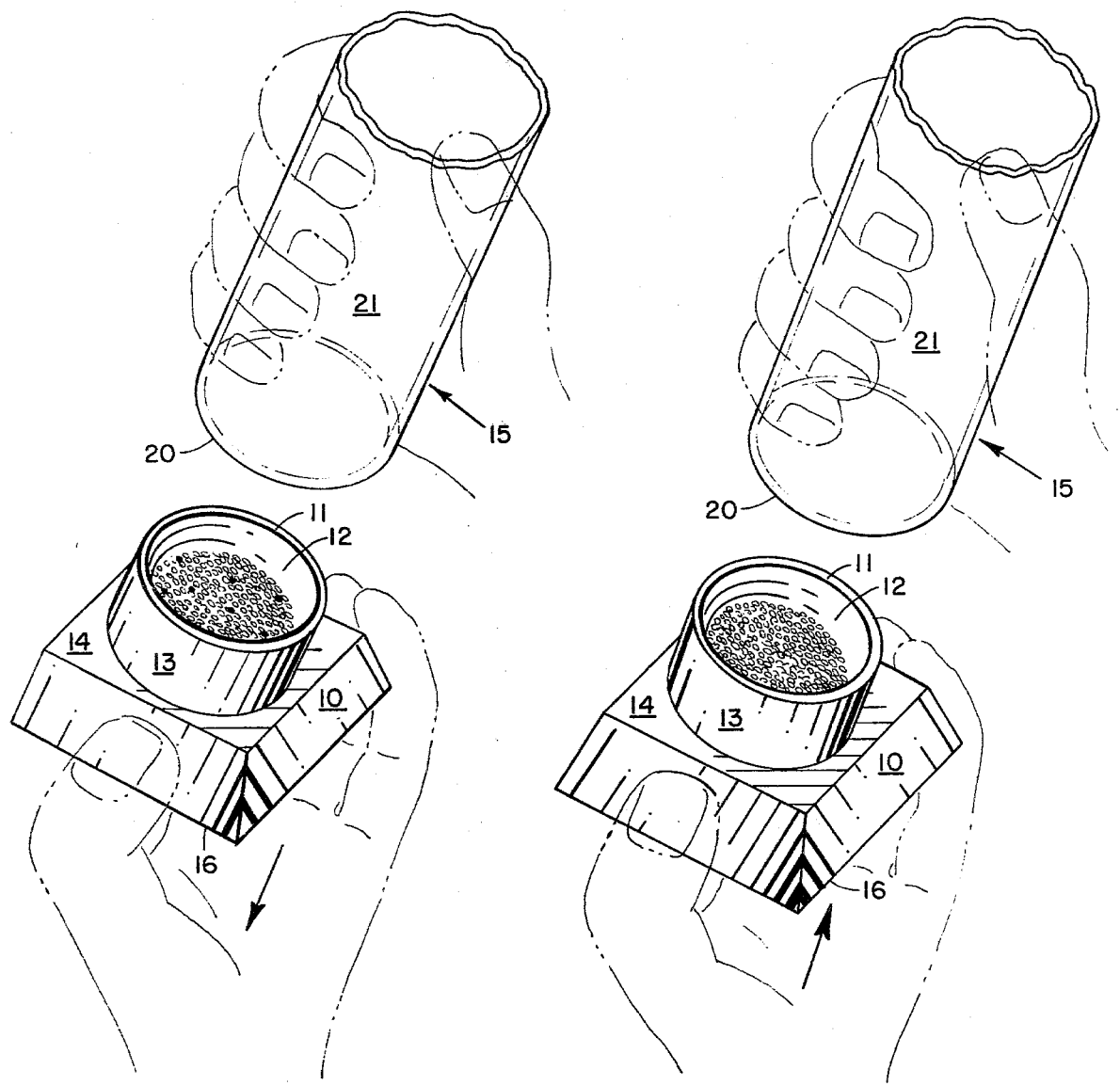
FIG. 3a is an illustration of a base and cylinder simulating a removing of a food cup containing eggs or larvae.
FIG. 3b is an illustration of a base and cylinder simulating the attaching of a fresh food cup.
Figure 4:
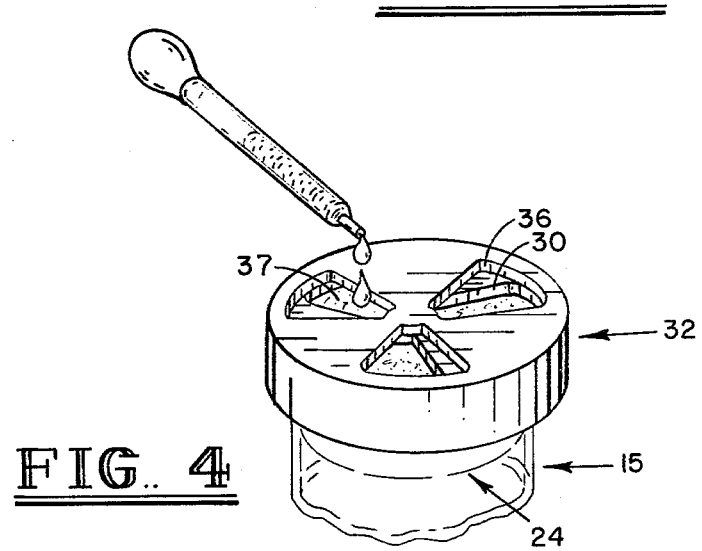
FIG. 4 is a symbolic illustration illustrating the process of anesthetizing the insects through the over and under cap.
Figure 5:
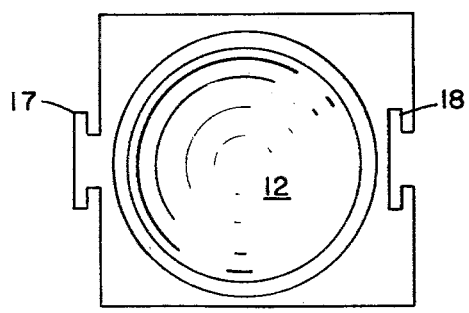
FIG. 5 illustrates an embodiment of the invention utilizing clip constructed in a base with a clip slot adapted to engage the clip of an adjacent base.
Figure 6:
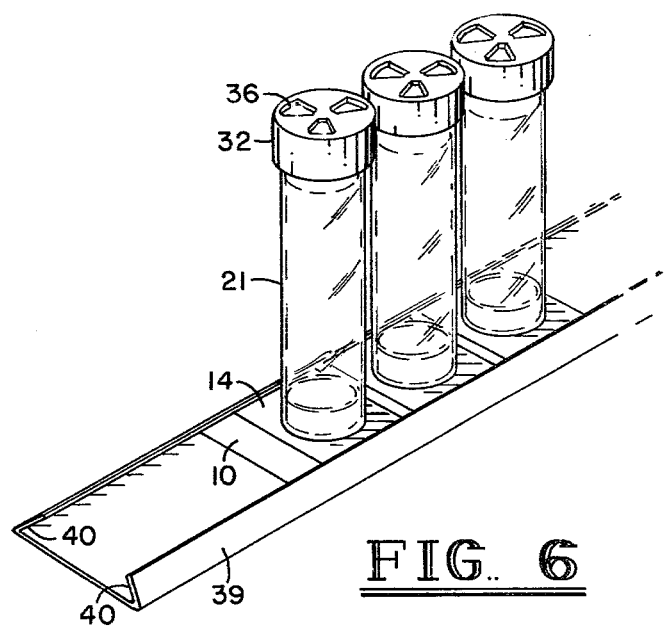
FIG. 6 is an illustration of a base retainer designed to receive and engage a series of bases by means of a base lip groove.

The device of this invention might be constructed of a wide variety of materials. However, for ease of production some form of plastic undoubtedly would be preferable. Construction might be made by either injection molding or vacuum molding. The base structure 10 might very well be cast or pour molded in the solid configuration. In the molded cup stamping or vacuum molding process might be preferable. Plastics such as acrylic or polyvinyl chloride might be utilized in constructing the base 10. The base 10 has a configuration generally as illustrated in FIG. 1 and includes a food cup 12 which is a dish-like, arcuate container at the upper edge of the base. The base is constructed with a flange 11 at its upper edge to prevent insects or food collecting on the edge of the cylindrical sleeve 13 which terminates in a cylinder stop 14. This structure is designed for generally receiving in a telescoping or sleeve-like engagement of cylinder of two or three inches in diameter and eight to twelve inches long would be a workable dimension for stock cultures; smaller $\frac{3}{4}''$ to $1\frac{1}{4}''$ for genetic crosses; the larger being too bulky and in inexperienced hands could lose all the insects. One of the principal differences between the structure of this invention and the prior art, to the best of the knowledge of your applicant, is in a structure of the base 10 and the food cup 12. Base 10 is constructed with a flared edge at its bottom comprising a base lip 16. In one embodiment, the base is constructed with a projecting clip 17 which engages a clip slot 18 in an adjacent base structure. In assembling the device into individual compartments, base 10 receives cylinder 15. The bottom edge of the cylinder is referred to as cylinder base 20 which slides over and snuggly engages cylinder sleeve 13 with the cylinder base 20 and contacting and firmly resting on cylinder stop 14. The elongated transparent edges of cylinder 15 are designated as cylinder side wall 21. The upper edge of the structure comprises cylinder top 22 which receives the cylinder undercap 24. The cap-like structure utilized on this device would preferably be constructed or molded from some resilient type plastic such as polyvinyl chloride or any of a wide variety of plastics having some resilient or flexible-like properties. The undercap 24 is constructed with a slightly elongated cap sleeve 25 which projects into cylinder 15 much in the same fashion as the cylinder sleeve 13 engages the outer edge of base 10. The undercap is constructed with a cap stop 26 which contains the undercap 24 in a stopper-like engagement in the cylinder top 22. It is preferable that the undercap 24 be constructed with a cap recess 27 terminating at its bottom edge in cap inner lip 28. This structure is desirable in that it facilitates retaining of the cotton bail 37 or other type fibrous material enclosing in a porous manner the apertures in the undercap 24. This fiber stopper also assists in anesthetizing of insects in the container if such procedure is desired in laboratory procedures. Undercap 24 is constructed normally with a series of undercap slots which are pie shaped or triangular apertures, normally three in number. The materials utilized in constructing the overcap 32 are normally semi-flexible plastics such as previously described in regard to the undercap 24. The overcap 32 is of a lid-like configuration comprising overcap sides 33 with an overcap lip 34 and is of such dimensions as to snugly slide over and engage or encase undercap 24. Overcap 32 is also preferably constructed with a series of three pie shaped or triangular slots having a compatible configuration with the undercap slots 30. When the overcap 32 is rotated, the overcap slots 36 and the undercap slots 30 are staggered, resulting in enclosure of the top of the container. A cotton ball 37 may be inserted into the undercap recess 27 to facilitate the closing of the top of the container. In laboratory use of the device of this invention, it is frequently desirable to interconnect a series of these containers. One method of accomplishing this is to utilize an elongated base retainer 39 which is formed with base lip groove 40 at each edge, as illustrated in FIG. 6. With this structure, a series of bases 10 may slidably engage this base retainer 39. The principal advantages of this device over the prior art is the flexibility of utilization in replacing the bases 20 containing the food cups 12; particularly in studies of the fruit fly, which is widely utilized in laboratories for genetic studies. The food cup bearing the larvae of the fruit fly, FIG. 3a, may be removed and replaced with a fresh food cup, FIG. 3b. The removed food cup 12 can be attached to another cylinder 15 for isolating a new generation of fruit flies. The control of succeeding generations in an isolated environment is facilitated by the structure of base 10 or food cup 12 with the series of cylinders 15 and undercap 24 or overcap 32 means. The manner in which the structural components of these devices are assembled and retained is wherein the flexibility of this composite structure resides.

OPERATION OF THE DEVICE

The operation of the device is rather self-evident in that the composite structure consisting of the base 10 bearing food cup 12 is assembled with cylinder 15 and enclosed with undercap 24 and/or an overcap 32. Again, with either of these structures, a cotton ball 37 or other fibrous material might be utilized. Food cup 12 is filled with a suitable food media after which insects, such as fruit flies, are placed in the cylinder 15. The flies feed on the food in addition to depositing their eggs. These eggs hatch into larvae at which time the base 10 with food cup 12 may be removed and attached to a new cylinder 15 and a fresh food cup 12 attached to the old cylinder still retaining the flies. The characteristic of most insects is that when they are disturbed they will migrate upward in the cylinder 15 and tend to rest and remain on the inner surface of undercap 24 or within the cap recess 27. The dimensions of the structure of this invention are not considered critical. The device may be made essentially in any dimension desired; however, prototype models of the device were constructed around cylinder 15 having a diameter of more or less one inch and four to six inches in length with the bases 10, food cups 12, and undercaps 24 and overcaps 32 having compatible or mating dimensions.

What is desired to be claimed is all embodiments and modifications of this invention not departing from the equivalents of the scope of the appended claims.

I claim:
1. An insect study station comprising:
   a. a base having a configuration adapted to telescopically engage and detachably retain an elongated cylinder,
   b. a cylinder having a base end and a top end, the base end of said cylinder telescopically engaging said base,
   c. a cap means enclosing the top end of said cylinder, said cap means further comprising:

(1) an undercap having constructed in its outer diameter,
(2) a cap sleeve penetrating and telescopically engaging said top end of said cylinder,
(3) said cap sleeve terminating in a cap stop,
(4) the interior of said undercap comprising a cap recess adapted to receive and retain a cotton ball,
(5) a multiplicity of apertures dispersed adjacent the periphery of said undercap,
(6) an overcap telescopically engaging and encasing said undercap,
(7) a multiplicity of apertures dispersed adjacent the periphery of said overcap, and
(8) the dispersal and spacing of said apertures in said overcap and said undercap being such as to provide for an open configuration when the apertures are aligned and a closed configuration when the apertures are staggered,
d. an indentation constructed in said base comprising a food cup opening into said cylinder.

2. The invention of claim 1 further comprising a multiplicity of bases and cylinders detachably engaging a base retainer.

3. The invention of claim 1 wherein said base further comprises:
a. a sleeve constructed in the outer perimeter of said base, said sleeve constructed to telescopically engage and retain said cylinder,
b. said food cup constructed internal of said sleeve and concentric therewith,
c. a cylinder stop concentric with said sleeve, said stop contacting and firmly supporting the base end of said cylinder.

4. An insect study station comprising:
a. a base having:
(1) a sleeve constructed in the outer perimeter of said base, said sleeve constructed and adapted to telescopically receive and retain a cylinder,
(2) a food cup constructed internal of said sleeve and concentric therewith,
(3) a cylinder stop constructed concentric with said sleeve, said stop constructed and adapted to firmly contact and support a cylinder;
b. a cylinder having a base end and a top end, the base end of said cylinder telescopically engaging said base,
c. an undercap enclosing the top end of said cylinder, said undercap further comprising:
(1) a cap sleeve penetrating and telescopically engaging said top end of said cylinder,
(2) said cap sleeve terminating in a cap stop, and
(3) the interior of said undercap comprising a cap recess adapted to receive and retain a cotton ball;
d. an overcap telescopically engaging and encasing said undercap,
e. a multiplicity of apertures dispersed adjacent the periphery of said undercap and said overcap, the spacing of said apertures in said overcap and said undercap being such as to provide for an open configuration when the apertures are aligned and a closed configuration when said apertures are staggered.

5. The invention of claim 4 further comprising a multiplicity of bases and cylinders detachably engaging a base retainer.

* * * * *